US008486901B2

(12) United States Patent
Lin

(10) Patent No.: US 8,486,901 B2
(45) Date of Patent: Jul. 16, 2013

(54) SODIUM CHANNEL BLOCKING COMPOUNDS TETRODOTOXIN GALACTOPYRANOSIDES

(75) Inventor: Weiyang Lin, Kwai Chung (HK)

(73) Assignee: Wex Medical Limited, Wachai (HK)

( * ) Notice: Subject to any disclaimer, the term of this patent is extended or adjusted under 35 U.S.C. 154(b) by 12 days.

(21) Appl. No.: 13/258,529

(22) PCT Filed: Mar. 26, 2010

(86) PCT No.: PCT/CA2010/000470
§ 371 (c)(1), (2), (4) Date: Jan. 6, 2012

(87) PCT Pub. No.: WO2010/111777
PCT Pub. Date: Oct. 7, 2010

(65) Prior Publication Data
US 2012/0101054 A1 Apr. 26, 2012

Related U.S. Application Data
(60) Provisional application No. 61/211,471, filed on Mar. 30, 2009.

(51) Int. Cl.

| | |
|---|---|
| ***A01N 43/04*** | (2006.01) |
| ***A01N 43/58*** | (2006.01) |
| ***A61K 31/70*** | (2006.01) |
| ***A61K 31/50*** | (2006.01) |
| ***C07H 17/02*** | (2006.01) |
| ***C07D 491/00*** | (2006.01) |

(52) U.S. Cl.
USPC ............. 514/32; 514/248; 536/17.4; 544/247

(58) Field of Classification Search
None
See application file for complete search history.

(56) References Cited

U.S. PATENT DOCUMENTS 6,552,191 B1 * 4/2003 Zhou et al. .................... 544/247

* cited by examiner

*Primary Examiner* — Traviss C McIntosh, III
(74) *Attorney, Agent, or Firm* — Fish & Richardson P.C.

(57) ABSTRACT

Novel sodium channel blocking compounds tetrodotoxm galactopyranosides of formula I were isolated and purified by HPLC and identified further through IR, NMR, GC, and MS. The compounds have a galactopyranosyl moiety attached to C11 of tetrodotoxin and retain the analgesic activity of the latter. Pharmaceutical compositions and medical uses thereof are further disclosed.

(I)

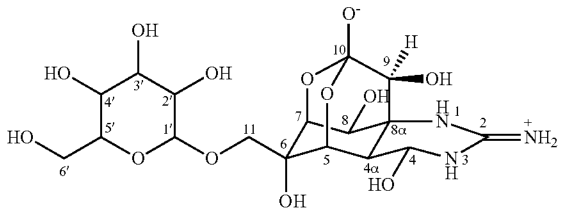

17 Claims, 7 Drawing Sheets

Tetrodotoxin (1a) and its tautomers in dilute acid solution

Tetrodotoxin (1a) Hemilactal (1b) Hydroxy-lactone (1c)

Inter-conversion between TTX and 4, 9-anhydro-TTX

TTX 4-epi-TTX 4,9-anhydro-TTX 11-(D-galactopyranosyl)-TTX (the hemilactal form) and its lactone form in equilibrium Impurity profile of a typical batch of Tetrodotoxin drug substance HPLC chromatogram of purified 11-galactopyranosyl-TTX ("Impurity A")

High Resolution Mass Spectrum of 11-galactopyranosyl-TTX

Infrared spectrum of 11-galactopyranosyl-TTX

Peak finding results for: Impurity A(21506001)
Frequency: 400.00 - 4000.00, threshold: 87.183, sensitivity: 50.00
Peak finding result table:

| Peak# | 1 | 2 | 3 | 4 | 5 | 6 | 7 | 8 | 9 | 10 | 11 | 12 | 13 | 14 | 15 | 16 | | |
|---|---|---|---|---|---|---|---|---|---|---|---|---|---|---|---|---|---|---|
| Position | 3342.11 | 1668.00 | 1602.58 | 1529.18 | 1408.81 | 1362.86 | 1334.90 | 1257.02 | 1205.21 | 1067.24 | 963.33 | 912.77 | 823.50 | 755.58 | 609.87 | 509.03 | | |
| Height | 5.006 | 5.024 | 17.569 | 38.841 | 19.483 | 13.613 | 12.444 | 17.670 | 14.973 | 2.963 | 19.735 | 9.600 | 29.804 | 26.119 | 21.817 | 22.452 | | |

$^1$H NMR spectra of 11-galactopyranosyl-TTX (a), D-galactose (b) and D-glucose (c)

GC chromatograms of D-glucose (a), D-galactose (b), 11-galactopyranosyl-TTX (c), and Tetrodotoxin (d)

SODIUM CHANNEL BLOCKING COMPOUNDS TETRODOTOXIN GALACTOPYRANOSIDES

RELATED APPLICATIONS

This application is the national phase under 35 U.S.C. 371 of International Application number PCT/CA2010/000470, filed on Mar. 26, 2010, which claims the benefit of U.S. Provisional Application No. 61/211,471, filed Mar. 30, 2009.

FIELD OF THE INVENTION

This invention relates to the purification and/or isolation of novel sodium channel blocking compounds, and methods of using same.

BACKGROUND OF THE INVENTION

Many sodium channel blocking compounds have been previously identified and purified. For example, tetrodotoxin ("TTX"), also known as Ti Qu Duo Xin, Puffer Fish toxin, maculotoxin, spheroidine, tarichatoxin, tetrodontoxin, fugu poison and TTX (The Merck Index, 12th Ed. p 1578 (1996)), is a biological toxin found in puffer fish (Tetradontiae). The chemical name is octahydro-12-(hydroxymethyl)-2-imino-5, 9:7,10a-dimethano-10aH-[1,3]dioxocino[6,5-d]pyrimidine-4,7,10,11,12-pentol with a molecular formula $C_{11}H_{17}N_3O_8$ and a molecular weight of 319.27. TTX is a potent non-protein neurotoxin and an indispensable tool drug for the study of neurobiology and physiology. TTX is a marine organic toxin which is mainly found in testicles, ovaries, eggs, livers, spleens, eyeballs, and blood of puffer fish as well as in diverse animal species, including goby fish, newt, frogs and the blue ringed octopus and even in marine algae. It is a known substance and production processes are known. Usually TTX is extracted from marine organisms (e.g. JP 270719 Goto and Takashi). Numerous extraction methods have been disclosed, for example, in U.S. Pat. No. 6,552,191, U.S. Pat. No. 6,478,966, U.S. Pat. No. 6,562,968 and US 2002/0086997, all hereby incorporated herein by reference. Synthesis of TTX has also been described and is well known to those skilled in the art (Kishi, Y. et al. *J. Am. Chem. Soc.* 1994, 94:9217-9221; Ohyabu, N. et al. *J. Am. Chem. Soc.* 2003, 125:8798-8805; and Hinman, A. et al. *J. Am. Chem. Soc.* 2003, 125:11510-11511).

TTX is known to be a highly potent and specific sodium channel blocker. Its biological activities and pharmacological properties have been the subject of numerous reviews, for example, Kao, *Pharmacol. Rev.* 18:997-1049 (1966); Tu, Anthony (Ed.) Handbook of Natural Toxins, Vol. 3: Marine Toxins and Venoms, pp. 185-210 (1988); and Narahashi, *J. Toxicol.* 20:67-84 (2001), all hereby incorporated by reference.

The use of TTX in pain management and treatment of drug addiction has been disclosed in, for example, WO 2002/022129 (Dong et al), CN 1,145,225 (Wang, et al), U.S. Pat. No. 5,846,975 (Pan et al), and U.S. Pat. No. 6,326,020 (Kohane et al). U.S. Pat. No. 6,407,088 to Dong et at describes the systemic application of tetrodotoxin in combination with suitable pharmaceutical vehicles to alleviate pain. U.S. Pat. No. 6,030,974 to Schwartz, et at describes a method of producing local anesthesia in a mammal experiencing pain in an epithelial tissue region. The method includes topically administering to the region, in a suitable pharmaceutical vehicle, an effective dose of a long-acting sodium channel blocking compound. Adams, et al., U.S. Pat. Nos. 4,022,899 and 4,029,793 pertain to a local anesthetic composition of tetrodotoxin or deoxytetrodotoxin, and another compound, generally a conventional local anesthetic compound or a similar compound having nerve-blocking properties.

Although TTX is safe and effective in treatment of various types of pain and drug addiction, TTX needs careful handling because of its pharmaceutical profile including the high level of toxicity and unique dosage window applicable to ensure safe and effective treatment with TTX. Additionally, not all patients respond well to TTX. Therefore alternative sodium channel blocking compounds that have unique properties and may have a different pharmaceutical profile would provide a useful alternative to treat and/or manage pain and/or drug addiction and thus would be desirable.

SUMMARY OF THE INVENTION

It is an object of the present invention to obviate or mitigate at least one or more of the disadvantages of previous sodium channel compounds, including TTX, by purifying a previously unidentified sodium channel blocker which has been surprisingly found to have utility in pain management.

In a first aspect, the present invention provides a purified compound of Formula I, or the pharmaceutically acceptable salt, solvate, or hydrate form thereof, wherein the substituent at C-11 is a galactoside.

(I)

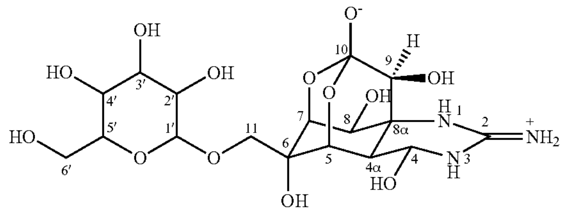

In another aspect the compound is D-galactopyranosyl-TTX as represented by Formula I-a, in yet another aspect the compound is L-galactopyranosyl-TTX as represented by Formula I-b. In yet another aspect the compound is a mixture of D-galactopyranosyl-TTX and L-galactopyranosyl-TTX. In yet another aspect, the mixture is comprised of a molar excess of D-galactopyranosyl-TTX. In yet another aspect, the mixture is comprised of a molar excess of L-galactopyranosyl-TTX. In yet another aspect, the mixture is a racemic mixture.

One or more compounds of this invention can be isolated and purified from puffer fish, goby fish, newt, frogs, blue ringed octopus or marine algae. The compounds may be used for preparation of a medicament to treat pain, and may be formulated using the addition of one or more pharmaceutically acceptable excipients.

One or more compounds of the invention can be used, optionally with one or more pharmaceutically acceptable excipients, for the preparation of a medicament for the treatment of pain, including neuropathic pain, hyperalgesia, allodynia, acute pain, chronic pain, musculoskeletal pain, visceral pain, inflammatory pain and cancer pain. One or more compounds of the invention may, optionally with one or more pharmaceutically acceptable excipients, be used for the preparation of a medicament to treat drug dependancy.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

Embodiments of the present invention will now be described, by way of example only, with reference to the attached Figures, wherein.

DETAILED DESCRIPTION

Definitions

Figure 1:
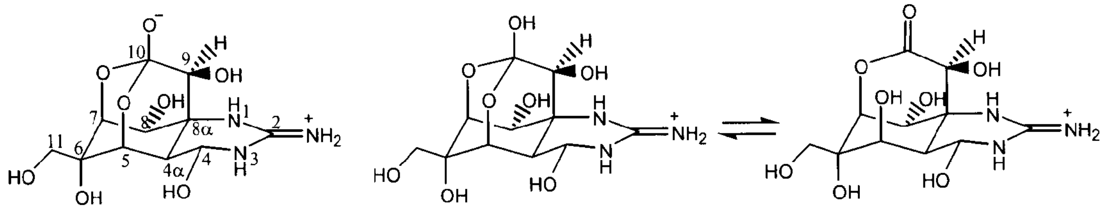
FIG. 1 illustrates the sodium channel blocker tetrodotoxin (TTX) and its tautomers in dilute acid solution.

"Isolated" when referring to a compound, as used herein, means isolated away from other chemicals, whether said other chemicals are chemical precursors used when chemically synthesizing said compounds, or other chemicals existing with said compound of interest in nature.

"Pain" is defined by the International Association for the Study of Pain (IASP) as "an unpleasant sensory and emotional experience associated with actual or potential tissue damage, or described in terms of such damage". The term "pain" as used herein means all forms of pain, including but not limited to acute pain, chronic pain, centrally and peripherally derived neuropathic and non-neuropathic pain, somatic pain, nociceptive pain, allodynia, causalgia, hyperpathia, hyperalgesia, hyperesthesia, neuritis, and all other conditions and symptoms which would be considered either colloquially or technically to be "pain". The artisan of ordinary skill in pain management recognizes that pain may arise from many different causes, be expressed by many different physiological mechanisms, and may be perceived by patients in many different ways.

"Pharmaceutically acceptable salt" means a salt of a compound suitable for pharmaceutical formulation and can include an acid addition salt, such as a sulfate, hydrobromide, tartrate, mesylate, maleate, citrate, phosphate, acetate, pamoate (embonate), hydroiodide, nitrate, hydrochloride, lactate, methylsulfate, fumarate, benzoate, succinate, mesylate, lactobionate, suberate, tosylate, and the like. The salt can also be a calcium salt, potassium salt, magnesium salt, meglumine salt, ammonium salt, zinc salt, piperazine salt, tromethamine salt, lithium salt, choline salt, diethylamine salt, 4-phenylcyclohexylamine salt, benzathine salt, sodium salt, tetramethylammonium salt, and the like.

"Pharmaceutically acceptable hydrate" refers to a compound of the invention, or a salt thereof, that further includes a stoichiometric or non-stoichiometric amount of water bound by non-covalent intermolecular forces.

"Pharmaceutically acceptable solvate" means an association of one or more solvent molecules and a compound of the invention. Examples of solvents that form pharmaceutically acceptable solvates include, but are not limited to, water, isopropanol, ethanol, methanol, DMSO, ethyl acetate, acetic acid, and ethanolamine.

"Purified" means having separated a compound of interest from other contaminating molecules, including other small molecules (e.g. TTX) and/or macromolecules (e.g. proteins, nucleic acids and the like), in a manner which increases the percentage of the compound of interest when compared to the percentage of the other contaminating molecules subsequent to such separation, such that the compound of interest is present in greater than 10%, 20%, 30%, 40%, 50%, 60%, 70%, 75%, 80%, 85%, 90%, 95%, 96%, 97%, 98%, 99% w/w when compared with other contaminating molecules. It is understood that the compound of interest may include stereoisomers, including enantiomers and distereomers and/or any or all of the tautomeric forms of the compound of interest, and that these are not necessarily considered contaminating molecules when referring to purification as described herein.

"Stereomerically pure" means a compound that is substantially free of other stereoisomers of that compound. For example, a stereomerically pure compound of the invention having one chiral center, or a composition thereof, will be substantially free of the opposite enantiomer of the compound. A stereomerically pure compound of the invention having two chiral centers, or a composition thereof, will be substantially free of other diastereomers of the compound. A typical stereomerically pure compound comprises greater than about 80% by weight of one stereoisomer and less than about 20% by weight of other stereoisomers, more preferably greater than about 90% by weight of one stereoisomer and less than about 10% by weight of the other stereoisomers, even more preferably greater than about 95% by weight of one stereoisomer and less than about 5% by weight of the other, and most preferably greater than about 97% by weight of one stereoisomer and less than about 3% by weight of the other stereoisomers. As used herein and unless otherwise indicated, the term "stereomerically enriched" means a compound of the invention, or a composition thereof, that comprises greater than about 60% by weight of one stereoisomer, preferably greater than about 70% by weight, more preferably greater than about 80% by weight of one stereoisomer. As used herein and unless otherwise indicated, the term "enantiomerically pure" means a stereomerically pure compound of the invention having one chiral center, or a composition thereof. Similarly, the term "stereomerically enriched" means a stereomerically enriched compound of the invention having one chiral center, or a composition thereof.

"Therapeutically effective amount" means that amount of active compound(s) or a pharmaceutical composition comprising an active compound(s) that elicits the biological or medicinal response in a tissue system, animal or human sought by a researcher, veterinarian, medical doctor or other clinician, which response includes alleviation of the symptoms of the disease or disorder being treated. The specific amount of active compound(s) or pharmaceutical composition needed to elicit the biological or medicinal response will depend on a number of factors, including but not limited to the disease or disorder being treated, the active compound(s) or pharmaceutical agent(s) being administered, the method of administration, and the condition of the subject.

"Treating" or "treatment" of a pain includes: (1) preventing pain, i.e., causing the clinical symptoms of pain not to develop in a mammal that may be exposed to or predisposed to experiences normally resulting in pain; (2) inhibiting or reducing the amount, scope or progression of pain, i.e., arresting or reducing or eliminating the amount of pain, or the scope of pain or one or more symptoms of pain.

"Trace amounts" when used herein means containing less than 10%, less than 5%, less than 3%, less than 2%, less than 1% by weight when compared with the amount of another compound. It is understood that 11-galactopyranosyl-TTX (including any isomers, stereoisomers, enantiomers, disteremers and/or any or all of the tautomeric forms of the 11-galactopyranosyl-TTX) (also referred to as gTTX or 11-Gal-TTX herein) is found in "trace amounts" in preparations of crude TTX isolated from puffer fish. Depending upon the method of preparation of TTX, and or the source of the TTX, the amount of gTTX may vary, but the amount of gTTX is still less than 10%, less than 5%, less than 3%, less than 2%, less than 1% of the amount of TTX.

Specific Embodiments

Generally, the present invention provides isolated or purified novel sodium channel blocking compounds, and pharmaceutical compositions thereof, as well as uses of said compounds.

Compounds of Formula I are described herein:

(I)

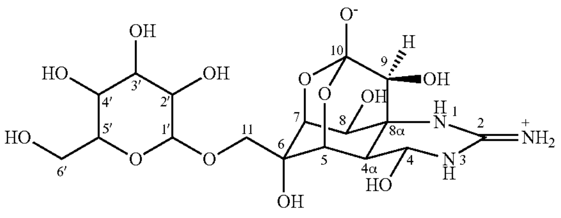

where the isomeric substituent at C-11 is galactoside the compounds may be isolated from nature, and purified, or partially purified.

In another embodiment, the 11-sugar is D-galactoside, corresponding to compound I-a, wherein the configuration at C-1' can be either R or S or a mixture thereof, including a racemic mixture thereof.

(I-a)

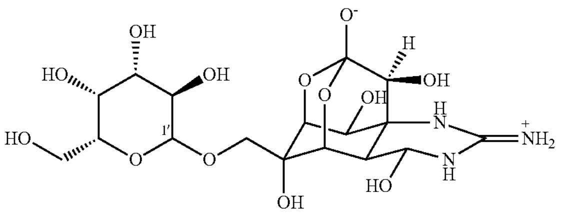

In another embodiment, the 11-sugar is L-galactoside, corresponding to compound I-b, wherein the configuration at C-1' can be either R or S or a mixture thereof, including a racemic mixture thereof.

(I-b)

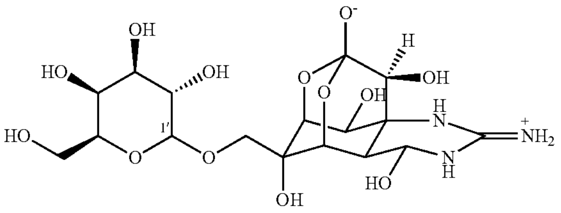

The 11-galactopyranosyl-TTX can be purified from puffer fish, goby fish, newt, frogs, blue ringed octopus and marine algae. 11-galactopyranosyl-TTX can also be purified from TTX which itself has been isolated from one of puffer fish, goby fish, newt, frogs, blue ringed octopus and marine algae.

One or more compounds of the invention can be used, optionally with one or more pharmaceutically acceptable excipients, for the preparation of a medicament for the treatment of pain, especially neuropathic pain, including hyperalgesia and allodynia; acute pain, chronic pain, musculoskeletal pain, visceral pain, inflammatory pain or cancer pain.

One or more compounds of the invention may also be used, optionally with one or more pharmaceutically acceptable excipients, for the preparation of a medicament to treat drug dependency.

Compounds contemplated herein are described with reference to both generic formulae and specific compounds. In addition, the invention compounds may exist in a number of different forms or derivatives, all within the scope of the present invention. These include, for example, tautomers and stereoisomers as discussed herein.

Tautomers and Stereoisomers

Figure 2:
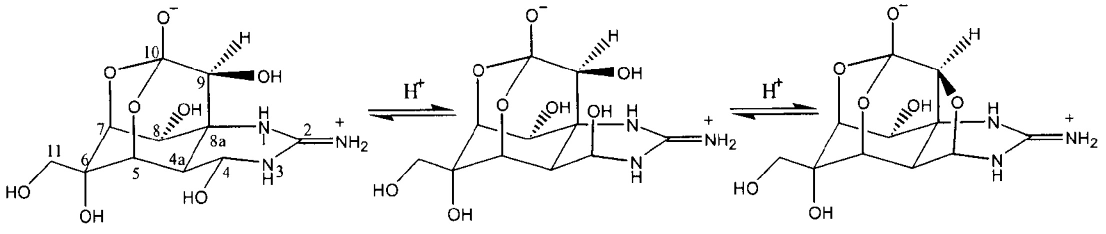
FIG. 2 illustrates the inter-conversion between TTX and 4,9-anhydro-TTX.

It is understood that compounds of the invention may exhibit tautomerism exhibited by TTX such as seen in FIG. 1 and FIG. 2. Thus the formulae provided herein expressly depict only one of the possible tautomeric forms. It is therefore to be understood that the formulae provided herein are intended to represent any tautomeric form of the depicted compounds and are not to be limited merely to the specific tautomeric form depicted by the drawings of the formulae.

For example, the structure of TTX, including its absolute configuration, was established in the early 1960s (Woodward R. B. *Pure applied chem.* 1964, 9:49-74; Mosher, H. S. et al. *Science* 1964, 144:1100-1110; Tsuda K. S. et al. *Chem. Pharm. Bull Jpn.* 1964, 12:1357-1374; Goto T. et al. *Tetrahedron* 1965, 21:2059-2088.) In the crystalline state, TTX exists entirely in the zwitterions form (FIGS. 1, 1*a*) and is stable indefinitely. In dilute acid solution, TTX exists in the protonated hemilactal form (FIGS. 1, 1*b*) which is in equilibrium with the hydroxy lactone forms (FIGS. 1, 1*c*) (Mosher H. S. *Ann. New York Acad. Sci.* 1986, 479:32-43; Yashumoto, T., et al. *J. Am. Chem. Soc.* 1988, 110:2344-2345; Yotsu-Yamashita M., *J. Toxicol.* 2001. 20:51-66.) TTX in powdered form is very stable, while in a mildly acidic solution, TTX can be slowly converted to 4,9-anhydro-TTX. The rate of conversion can be accelerated by heat or by increasing strength of the acidity. In an alkaline solution, TTX can be quickly degraded into 2 amino-6-hydroxymethyl-8-hydroxylquinazoline (C9 base).

It is also known that TTX in dilute acidic solution can slowly undergo epimerization of the hydroxyl group at position C4 to form 4-epi-TTX which is not stable and will undergo dehydration to 4,9-anhydro-TTX (FIG. 2). The dehydration process can be accelerated under heating and acidic conditions. Isolation of 4-epi-TTX and 4,9-anhydro- TTX has been reported and their chemical structures were elucidated (Nakamura, M. and Yasumoto T. *Toxicon.* 1985, 23:271-276; Kao C. Y. and Yasumoto T. *Toxicon* 1985, 23:725-729.) The relative lethal potencies of TTX, 4-epi-TTX and 4,9-anhydro-TTX to mice by i.p. injection were 4500, 710, and 92 mouse units/mg, respectively (Nakamura and Yasumoto Toxicon. 1985, 23:271-276.)

It is understood that compounds of Formula I, Formula I-a and Formula I-b undergo similar transformations as described above for TTX in solution. Formula I, Formula I-a and Formula I-b are intended to embrace each and all of the tautomeric forms, and in particular embrace 11-galactopyranosyl-TTX and all tautomeric forms of 11-galactopyranosal-TTX which may exist, and as would be understood by a person skilled in the art. By way of example, it is expected that tautomeric forms of compounds according to the invention would include tautomeric forms comparable with those which are adopted by TTX. See for example FIG. 3.

Likewise, the compounds according to the present invention may exist as stereoisomers, i.e. they have the same sequence of covalently bonded atoms and differ in the spatial orientation of the atoms. For example, compounds of the invention contain one or more chiral centers, and therefore, may exist in two or more stereoisomeric forms (e.g. enantiomers or diastereomers). Thus, such compounds may be present as single stereoisomers (i.e., essentially free of other stereoisomers), racemates, and/or other mixtures and combinations of enantiomers and/or diastereomers. In some embodiments, the compounds of the present invention are stereomerically pure having regard to at least one of the chiral centers. In other embodiments, the compounds of the present invention are stereomerically enriched having regard to at least one of the chiral centers.

Stereoisomers encompassed within the invention include D-11-galactopyranosyl-TTX, L-11-galactopyranosyl; racemic mixtures of D-11-galactopyranosyl-TTX and L-11-galactopyranosyl-TTX, and any of the above, where the configuration at C-1' is either R, S or mixtures thereof. Polymorphic crystalline forms and solvates are also encompassed within the scope of this invention.

It is recognized that some preparations of TTX have trace amounts of 11-galactopyranosyl-TTX. A purified preparation of 11-galactopyranosyl-TTX includes more than trace amounts of 11-galactopyranosyl-TTX as defined herein.

Pharmacology and Utility

It has been determined that like TTX, the compounds of the invention are also sodium channel blockers, and are useful for producing therapeutic effects mediated by blocking the functions of such sodium channels. For example, the compounds of the invention may be particularly useful in producing analgesia in mammals, including but not limited to (1) treatment of pain as defined herein, including various pains caused by burning, trauma, injuries from falls, fractures, contusions and strains, including pain for neuragia, myalgia and arthralgia; (2) treatment of pain caused by cancer such as, for example, liver cancer, rectal cancer, leiomyosarcoma, bone cancer, stomach cancer, lymphatic cancer, esophageal cancer, cancers in the genital organs, prostate cancer, digestive system cancer, stomach cancer, colon cancer, breast cancer, respiratory system cancer, lung cancer, bronchial cancer, urinary system cancer, lymphoma and skin cancer; and (3) producing prolonged local anesthetic effects and (4) producing prolonged systemic effects and (5) treating drug withdrawal (e.g. opiods).

The compounds of the invention may also be useful as antipruritic for winter skin itch, prurigo, thylacitis, itch mite and sarcoptic mite; asthma and pertusis abirritant; and antispasmodic for myospasm, gastrospasm and other kinds of spasms, particularly for tetanospasm (U.S. Pat. No. 5,846,975).

The agents useful in combination with compounds of this invention for producing prolonged local anesthetic effects may be selected from the group consisting of vasoconstrictors, adrenergic drugs, vanilloids, amphiphilic solvents, lipophilic solvents, glucocorticoids, and controlled or prolonged release formulations; said adrenergic drugs are selected from the group consisting of alpha agonists, beta-blockers, and mixed central-peripheral alpha-2 agonists, for examples, epinephrine, phenylephrine, propranalol, and clonidine; said vanilloid is selected from the group consisting of trans-8-methyl-N-vanillyl-6-nonenamide, N-vanillyl-nonanamide, beta-aminoethyl-substituted phenyl alkanamides, methylene substituted-N-phenylmethyl alkanamides, N-[(substituted phenyl)methyl]-cis-monounsaturated alkenamides, beta-aminoethyl-substituted phenyl compounds, N-[(substituted phenyl)methyl]diunsaturated amides, resinifera compounds, and derivatives and salts thereof; said glucocorticoid is selected from the group consisting of dexamethasone, cortisone, hydrocortisone, prednisone, beclomethasone, betamethasone, flunisolide, methyl prednisone, para methasone, prednisolone, triamcinolome, alclometasone, amcinonide, clobetasol, fludrocortisone, difluorosone diacetate, fluocinolone acetonide, fluoromethalone, flurandrenolide, halcinonide, medrysone, mometasone, and pharmaceutically acceptable salts and mixtures thereof In one aspect, the invention relates to the use of at least one compound of general Formula I wherein the substituent at C-11 is a galactoside. In yet another aspect, the invention relates to the use of compound encompassed by Formula I-a and/or Formula I-b. In yet another aspect, one or more compounds of the invention are combined with one or more pharmaceutically acceptable excipients, for the preparation of a medicament for the treatment of pain, including neuropathic pain, hyperalgesia, allodynia; acute pain, chronic pain, musculoskeletal pain, visceral pain, inflammatory pain or cancer pain.

In another aspect, the invention relates to the use of a compound of Formula I wherein the substituent at C-11 is galactoside, and/or compounds of Formula I-a, and/or Formula I-b and optionally one or more pharmaceutically acceptable excipients, for the preparation of a medicament for treating addiction to a drug/substance or dependency on a drug/substance, or ameliorating the effects of a de-addiction treatment from a drug/substance wherein said drug/substance is selected from morphine and other opioids, cocaine and its derivatives, *cannabis*, nicotine, amphetamines and other addictive drugs like phencyclidine, hallucinogens, benzodiazepines and barbiturates.

In a further aspect, the invention provides a composition for causing nerve blockade wherein the nerve blocking agent consists of at least one analog of tetrodotoxin of general Formula I wherein the substituent at C-11 is a galactoside and/or compounds encompassed by Formula I-a and/or Formula I-b and optionally one or more pharmaceutically acceptable excipients, in combination with an agent selected from the group consisting of vasoconstrictors, adrenergic drugs, vanilloids, amphiphilic solvents, lipophilic solvents, glucocorticoids, and controlled or prolonged release formulations, wherein the combination is effective to provide prolonged or modality selective nerve blockade in the absence of systemic toxicity Modes of Administration and Pharmaceutical Formulations Suitable modes of administration of the pharmaceutical composition include, but are not limited to, parenteral, subcutaneous, intravenous, intramuscular, interperitoneal, rectal, and vaginal administration. The term parenteral, as used herein, includes subcutaneous injections, and intravenous, intrathecal, intramuscular, and intrasternal injection or infusion techniques. A preferred mode of administration is systemic administration of a compound of this invention to the subject.

The pharmaceutically acceptable carriers described herein, for example, vehicles, adjuvants, excipients, and diluents, are well known to those who are skilled in the art and are readily available. Preferably, the carrier is chemically inert to a compound of this invention and has no detrimental side effects or toxicity under the conditions of use. Preferably, the pharmaceutically acceptable carrier is free of pyrogen. The pharmaceutically acceptable carriers which can be used include, but are not limited to, water, glucose, lactose, gum acacia, gelatin, mannitol, starch paste, magnesium trisilicate, talc, corn starch, keratin, colloidal silica, potato starch, and urea.

In general, compounds of Formula I, wherein the substituent at C-11 is galactoside including compounds of Formula I-a and/or Formula I-b, and/or mixtures thereof can be administered in therapeutically effective amounts via any of the usual and acceptable modes known in the art, either singly or in combination with another therapeutic agent. A therapeutically effective amount may vary widely depending upon the subject treated, the potency of the compound used, the particular mode of administration, and other factors. For example, therapeutically effective amounts of a compound of Formula I may range from 0.02 micrograms per kilogram body weight (μg/kg) per day to 20 μg/kg per day, typically 0.1 μg/kg/day to 5 μg/kg/day. Therefore, a therapeutically effective amount for an 80 kg human patient may range from 1.6 μg/day to 1.6 mg/day, typically 8 μg/day to 0.4 mg/day. For external administration, the active ingredient may be formulated within the range of, for example, 0.00001% to 60% by weight, and preferably from 0.001% to 10% by weight. In addition, the pharmaceutical composition can be administered on an intermittent basis, i.e., at daily, semi-weekly, or weekly intervals. It will be understood, however, that the specific dose level for a particular subject will depend on a variety of factors. These factors include the activity of the specific compound employed; the age, body weight, general health, sex, and diet of the subject; the time and route of administration and the rate of excretion of the drug; whether a drug combination is employed in the treatment; and, the severity of the particular disease or condition for which therapy is sought.

The pharmaceutical composition can be an injectable formulation. The requirements for effective carriers for injectable compositions are well known to those of ordinary skill in the art (see, e.g., Pharmaceutics and Pharmacy Practice, J. B. Lippincott Company, Philadelphia, Pa., Banker and Chalmers, eds., pages 238-250 (1982), and ASHP Handbook on Injectable Drugs, Toissel, 4th ed., pages 622-630 (1986)). Preferably, injectable compositions are administered intravenously. Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

The pharmaceutical composition can further comprise a pharmaceutically acceptable excipient. Excipients that may be used include one or more carriers, surface active agents, thickening or emulsifying agents, solid binders, dispersion or suspension aids, solubilizers, colorants, flavoring agents, coatings, disintegrating agents, lubricants, sweeteners, preservatives, isotonic agents, and combinations thereof. The selection and use of suitable excipients is taught in Gennaro, ed., *Remington: The Science and Practice of Pharmacy,* 20th Ed. (Lippincott Williams & Wilkins 2003), the disclosure of which is incorporated herein by reference.

The practice of this invention can be further understood by reference to the following examples, which are provided by way of illustration and not of limitation.

Purification

The present invention includes methods for purifying 11-(galactopyranosyl)-TTX, represented by Formula I, and/or Formula I-a, and/or Formula I-b as noted herein wherein each compound may exist as the R- or S-enantiomer at C-1' or a mixture thereof. It is anticipated that each compound represented by Formula I, Formula I-a, or Formula I-b, may as one or more stereoisomers or tautomers, for example, the compounds represented by Formula I, Formula I-a and Formula I-b may exist in equilibrium as between the hemilactal and lactone forms when formulated in acidic solutions. See for example FIG. 3.

Example 1

Isolation of 11-Galactopyranosyl-TTX from Crude TTX

Figure 4:
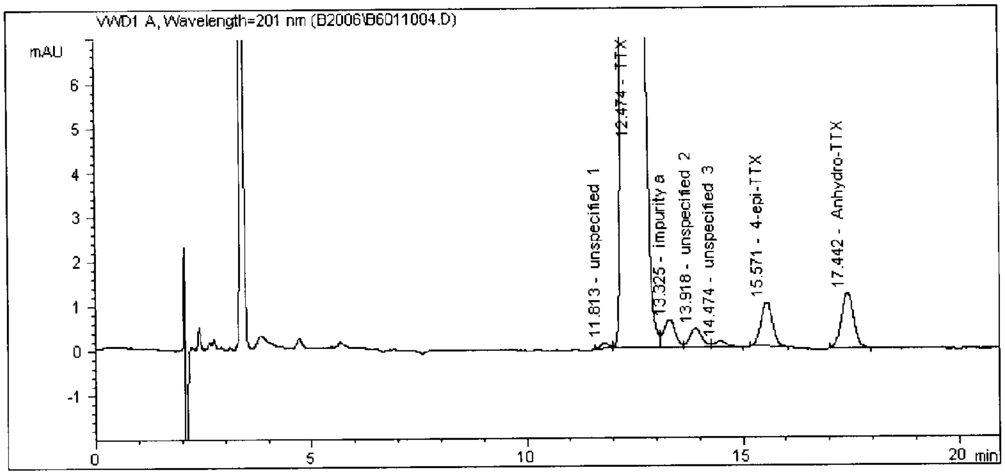
FIG. 4 illustrates the impurity profile of a typical batch of tetrodotoxin drug substance isolated from puffer fish.

Crude TTX extracted from ovaries of puffer fish following procedures previously described (Zhou, et al. U.S. Pat. No. 6,552,191) contains TTX with several minor components including known compounds such as 4-epi-TTX and 4,9-anhydro-TTX and compounds previously unknown, as shown in a typical HPLC chromatogram as shown in FIG. 4. The peak labeled "Impurity A", found in trace amounts in crude TTX, has been isolated and characterized as 11-galactopyranosyl-TTX (gTTX) as described below.

Methods

Isolation and purification of 11-galactopyranosyl-TTX from crude TTX (cTTX) was conducted by repeating several cycles of chromatographic fractionation on Bio-Gel P2 column and Source 15 RPC column.

(1) 8.2 g cTTX was dissolved in 80 mL of 2.5% TFA solution and was filtered through 0.22 μm syringe filter.

(2) The cTTX solution was loaded on a self-packed Bio-Gel P2 column and eluted with 0.01% acetic acid solution on the ÄKTA explorer 100 MPLC. Fractions collected by fraction collector were subjected to HPLC analysis. Fractions with enriched gTTX were combined and concentrated by a rotary evaporator.

(3) The concentrated solution from step (2) was passed through Bio-Gel P2 column again. Fractions with higher level of gTTX were combined and concentrated. Repeated the same purification process several more times until the chromatographic purity of gTTX is above 70%.

(4) The concentrated sample from step (3) was loaded on a self-packed Source 15 RPC column (3.5*27 cm) and eluted with 0.5 mM Sodium 1-Heptanesulfonate (SHS) and 0.03% trifluoroacetic acid (TFA). Collected the eluate corresponding to the peak of gTTX, adjust the pH to 5 with ammonia solution and concentrated to about 1 mL.

(5) The concentrate was mixed with 6 mL methanol, transfered to a centrifuge tube, adjusted pH to 8.5~9.5 with ammonia solution while stirring to precipitate gTTX, stored the solution at −20° C. for about 10 minutes.

gTTX was collected by centrifugation below −8° C., washed with methanol, and centrifugation/washing process repeated two more times. The precipitate was dried under vacuum at room temperature for 4 hours.

Results

Figure 5:
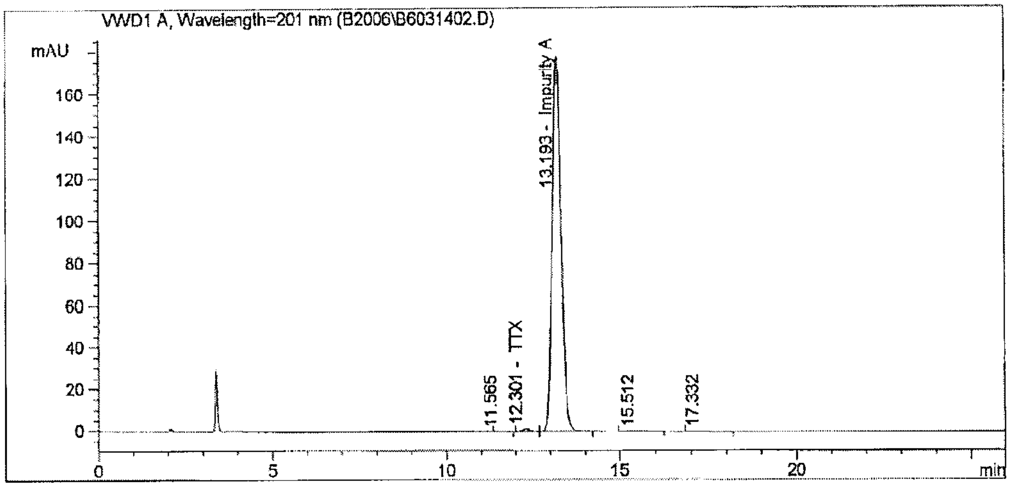
FIG. 5 illustrates an HPLC chromatogram of purified 11-galactopyranosyl-TTX.

The sample was analyzed by HPLC-UV (QC-006, rev#005). The result shows the chromatographic purity of gTTX is 99.1% (FIG. 5). Contaminating molecules in this purified sample included 0.63% TTX, 0.16% 4-epi-TTX and 0.11% 4,9-anhydroTTX as determined by HPLC.

Characterization of Isolated 11-Galactopyranosyl-TTX

The structure of the gTTX was confirmed based on HRMS, IR, $^1$H-NMR, $^{13}$C-NMR DEPT, gCOSY, gHSQC, TOCSY and gHMBC spectra analysis. From the interpretation of the spectroscopic studies, the compound was concluded to be 11-galactopyranosyl-TTX. The identity of the sugar moiety was confirmed by Gas Chromatography analysis of the trimethylsilyl derivatives of the degradation products under acidic conditions.

Methods

Infrared Spectroscopy 1 mg of sample was put into approximately 200 mg KBr powder (200 Mesh) that was dried under an IR lamp. The mixture was ground and mixed evenly in an agate mortar. The mixture was put into a pressing mold, placed in a pressing machine and loaded at a pressure of 6-7 tons for about 1 min. The film was then ready for IR spectroscopy.

Mass Spectrometry

Approximately 1 mg sample was removed and dissolved in 10 mL dilute acetic acid. The sample was then injected into the Bruker APEX™ FT-MS spectrometer and a spectrum taken.

NMR Spectrometry

Approximately 8-10 mg sample was dissolved in 0.5 mL of 4% $CD_3COOD$ solution, and a small amount of tetramethylsilane (TMS) added as an internal standard. The solution was transferred to an NMR sample tube and subjected to NMR analyses on Varian INOVA-501 NMR spectrometer. The signal of $CHD_2COOD$ at 2.06 ppm in $^1$H NMR and the signal of $^{13}CD_3COOD$ at 22.4 ppm in $^{13}$C NMR were used as references for the NMR spectra assignment.

Degradation and Derivatization (a) 1 mg of TTX, 11-galactopyranosyl-TTX, D-galactose or D-glucose was dissolved in 0.8 mL 0.2M HCl and each was mixed at room temperature for 10 min; (b) The solutions were subsequently lyophilized and re-suspended in 0.5 mL pyridine; (c) The solutions were derivatized using chlorotrimethylsilane (TMSCl) and hexamethyl disilazane (HMDS) as derivative agents; (d) The samples were centrifuged in a desktop centrifuge at 34,000 rpm for 2 min and the supernatants were subjected to GC analysis.

Gas Chromatography

Instruments: Agilent 6820Gas Chromatography; SPH-300 Hydrogen Generator; PEAK NM20ZAHigh Purity Gas Generator.

GC conditions: Carrier gas flow: High purity helium, 5 mL/min; Inlet Temperature, 250° C.; Split, 1:20; FID detector: Temperature: 280° C.; Column: Agilent DB-1, 15 m×0.53 mm×0.5 μm; Oven: 150° C., 5 min; 150-160° C., 5° C./min; 160° C., 13 min; 160-250° C., 40/min; 250° C., 7 min.

Results

Figure 6:
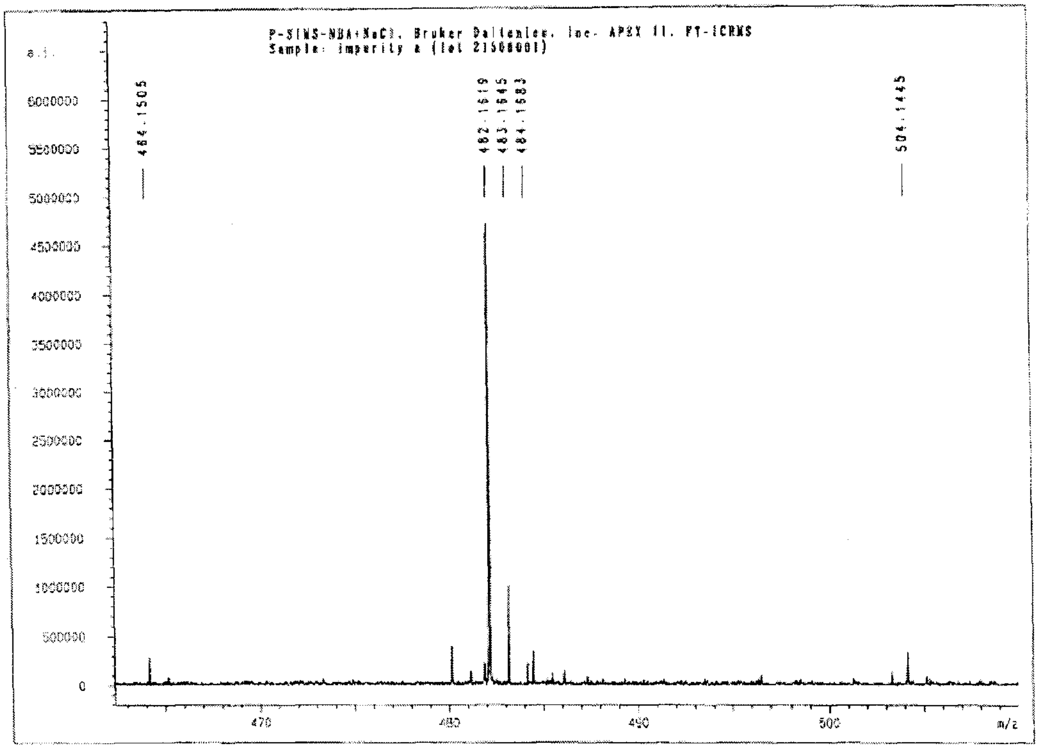
FIG. 6 illustrates a high resolution Mass spectrum of 11-galactopyranosyl-TTX.

Mass spectroscopy analysis: Mass spectrometry gave a $(M+H)^+$ ion at m/z 482.4 which is 162 higher than that of TTX (m/z 320), indicating that the molecule is not a common known TTX derivative. High Resolution Mass Spectrum (HRMS) analysis confirms the ion mass of "Impurity A" (m/z 482.1618, FIG. 6). Three compositions were predicted via calculation of the molecular ion mass based on the relative abundance of the isotopes (Table 1). It is unlikely that the molecule possesses "S" and the third composition has relative higher variation. Most likely the composition of $(M+H)^+$ ion is $C_{17}H_{28}N_3O_{13}$, an extra $C_6H_{10}O_5$ is found after subtracting the $(M+H)^+$ ion composition of TTX ($C_{11}H_{18}N_3O_8$), suggesting that "Impurity A" was a monosaccharide of TTX, such as glucose or galactose.

TABLE 1

Prediction of gTTX composition by HRMS

| | C | H | N | O | S | Mass | Error |
|---|---|---|---|---|---|---|---|
| Max | 25 | 50 | 5 | 15 | 1 | | |
| Min | 12 | 12 | 1 | 1 | 0 | | |
| 1 | 24 | 26 | 4 | 5 | 1 | 482.1618 | 8.23e−08 |
| 2 | 17 | 28 | 3 | 13 | 0 | 482.1616 | 4.58e−07 |
| 3 | 20 | 26 | 4 | 10 | 0 | 482.1643 | 5.10e−06 |

Figure 7:
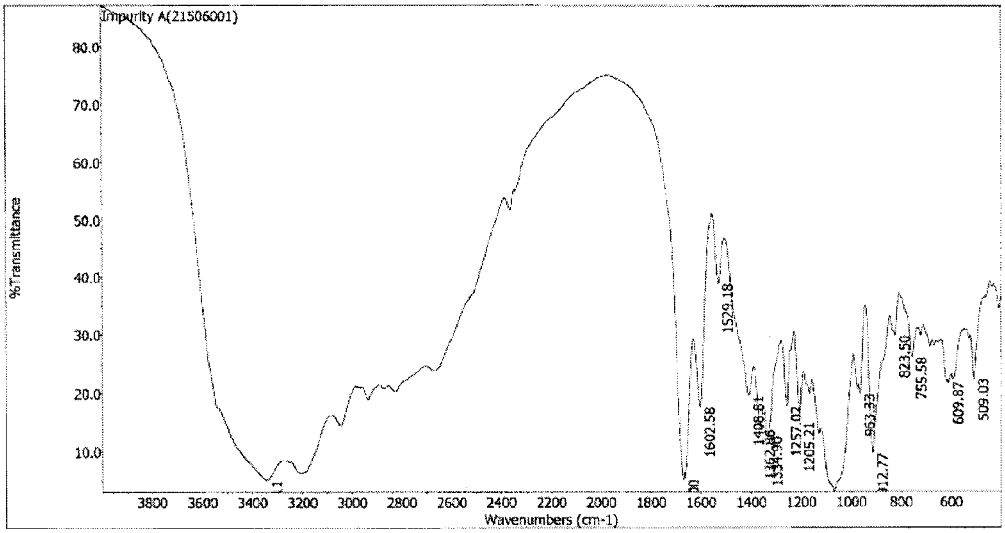
FIG. 7 illustrates an Infrared spectrum of 11-galactopyranosyl-TTX.

Infrared Spectroscopy Analysis:

The infrared spectrum of 11-galactopyranosyl-TTX was recorded in KBr using a FT-IR Nicolet-200 spectrometer. The sample was run as a KBr pellet between 4000~400 $cm^{-1}$ resolution and the IR spectrum is illustrated in FIG. 7. The resulting IR spectrum is similar to that of TTX. In addition to the strong absorption 3342 nm caused by the stretching vibrations of O—H and N—H in a number of —OH groups, the absorption around 1205, 1257 and 1335 nm can be attributed to the stretching vibration of the C—O of acetal group in polyformic acid structure and the asymmetric stretching vibration of C—O in numerous hydroxyl groups. This illustrates the existence of polyformic acid structure in the molecule. No special new functional group was identified. This information conforms to a monosaccharide of TTX.

Figure 3:
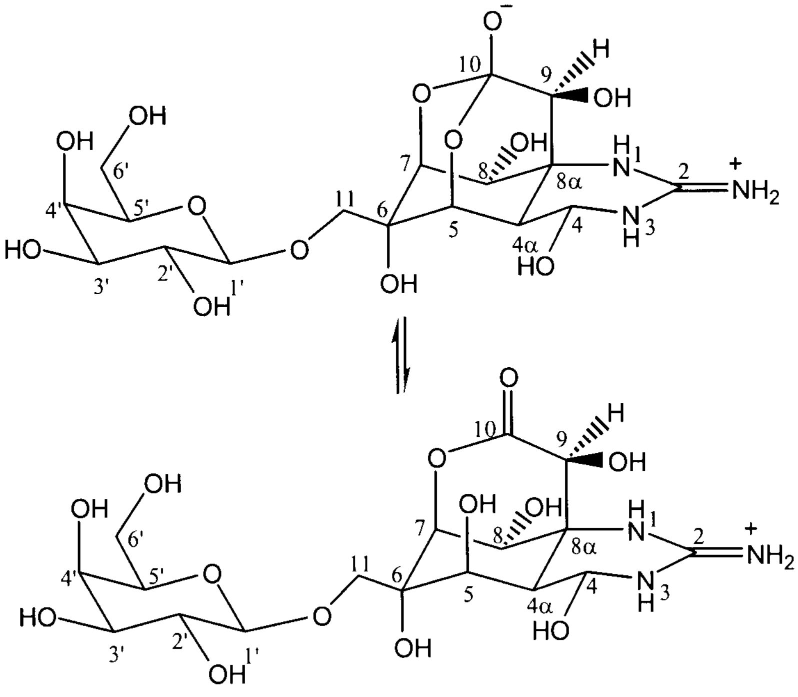
FIG. 3 illustrates 11-(D-galactopyranosyl)-TTX (hemilactal) and its lactone form.
Figure 8:
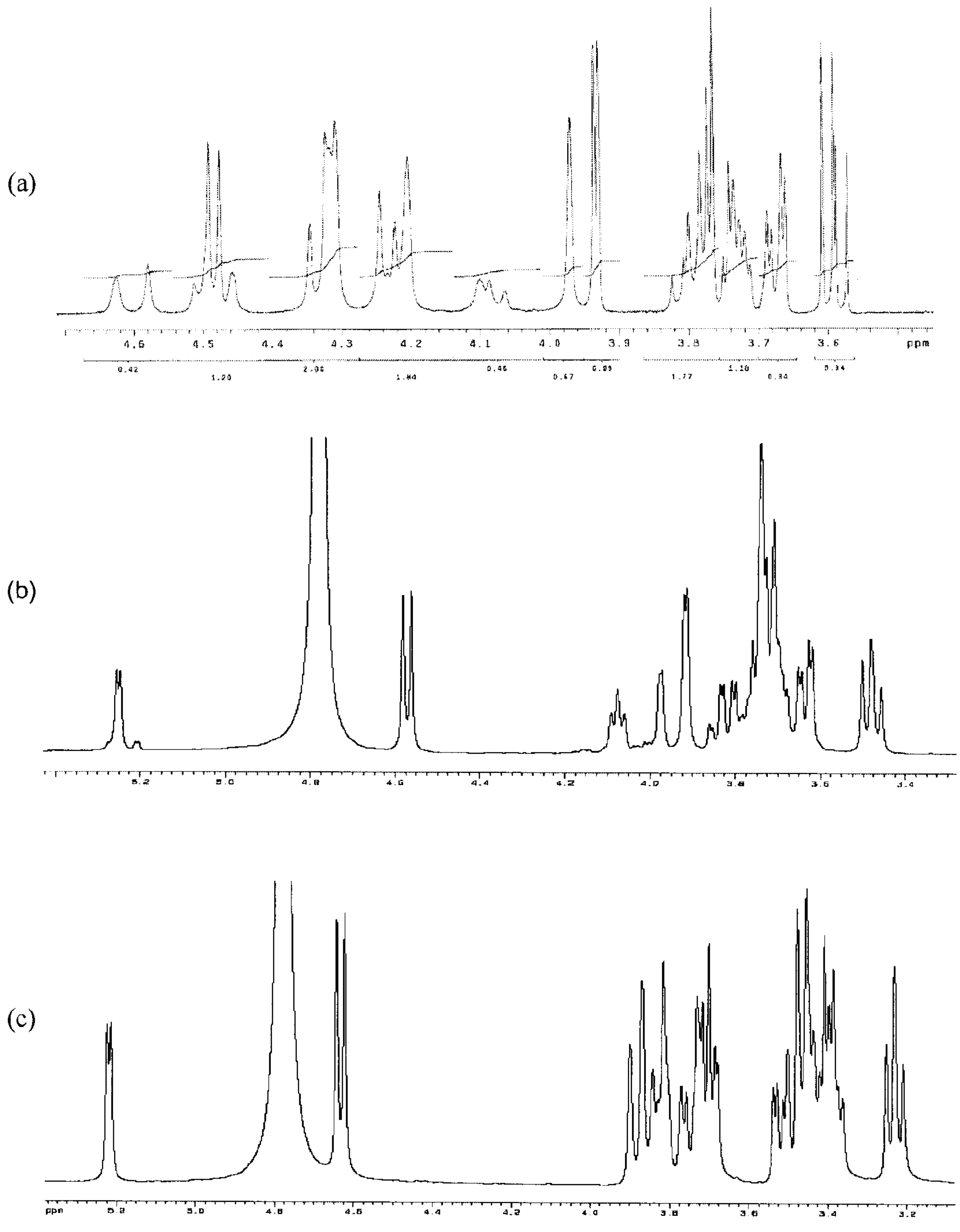
FIG. 8 illustrates $^{1}H$ NMR spectra of (a) 11-galactopyranosyl-TTX, (b) D-galactose and (c) D-glucose.

NMR Spectroscopy Analysis:

The $^1$H NMR spectrum showed a total of fourteen protons (FIG. 8). Eight of them can be assigned to TTX while the other six protons are attributed to the sugar moiety. The sharp doublet peaks at 5.50 ppm (d, J=9.50 Hz) were assigned to 4-H. The 4α-H signal appeared at 2.36 ppm as a doublet (J=9.50 Hz), coupled with 5-H at 4.31 ppm. The three singlet peaks at 3.91, 4.21 and 4.32 ppm can be assigned as 9-H, 7-H and 8-H respectively. Two doublet signals at 4.33 and 4.24 ppm (J=11.5 Hz) can be assigned to the germinal protons at C-11. The shift of the germinal protons at C-11 toward downfield suggests that $C_{11}$—OH is substituted with an electronic rich group. Several minor peaks resembling that of TTX lactone are present, indicating that 11-galactopyranosyl-TTX in dilute acetic acid solution also exists in equilibrium between hemilactal and lactone forms (FIG. 3). The relative peak intensity suggests that the ratio of the hemilactal and lactone forms of the 11-galactopyranosyl TTX is approximately 4:1, similar to the ratio of the hemilactal and lactone forms of TTX.

The extra protons signals detected at 3.6-4.2 ppm is attributed to the sugar moiety. The proton profile resembles that of D-galactose (FIG. 8) suggesting "Impurity A" is 11-galactopyranosyl-TTX. This identification was confirmed after a series of additional NMR studies, including DEPT, TOCSY, gHMBC, gCOSY and gHSQC.

Three quadruplet peaks at 3.59 ppm, 3.68 ppm and 3.78 ppm were assigned as 2'-H, 3'-H and 5'-H of Galactose. The sharp doublet peaks at 3.93 ppm (d, J=3.5 Hz) and 4.48 ppm (d, J=7.5 Hz) were assigned to 4'-H and 1'-H respectively. Two doublet signals at 3.76 and 3.80 ppm are attributable to the germinal protons at 6'-H. The $^{1}H$-NMR and $^{13}C$-NMR data of 11-galactopyranosyl-TTX is tabulated in Table 2.

TABLE 2

$^{1}H$ NMR assignment of 11-galactopyranosyl-TTX

| No | $\delta_C$ | $\delta_H$ |
|---|---|---|
| 2 | 157.0 | |
| 4 | 75.5 | 5.50 (1H, d, J = 9.50 Hz) |
| 5 | 73.0 | 4.31 (1H, s) |
| 6 | 71.5 | |
| 7 | 80.0 | 4.21 (1H, s) |
| 8 | 74.4 | 4.32 (1H, s) |
| 9 | 71.3 | 3.97 (1H, s) |
| 10 | 111.3 | |
| 11 | 74.3 | 4.33 (1H, d, J = 11.5 Hz) |
| | | 4.24 (1H, d, J = 11.5 Hz) |
| 4α | 41.0 | 2.36 (1H, d, J = 9.5 Hz) |
| 8α | 60.0 | |
| 1' | 106.5 | 4.48 (1H, d, J = 1.5 Hz) |
| 2' | 73.9 | 3.59 (1H, dd, J = 10.0 Hz, J = 7.5 Hz) |
| 3' | 75.6 | 3.68 (1H, dd, J = 10.0 Hz, J = 3.5 Hz) |
| 4' | 71.6 | 3.93 (1H, d, J = 3.5 Hz) |
| 5' | 78.2 | 3.73 (1H, dd, J = 8.0 Hz, J = 4.5 Hz) |
| 6' | 64.0 | 3.80 (1H, dd, J = 11.5 Hz, 8.0 Hz) |
| | | 3.76 (1H, dd, J = 11.5 Hz, 4.5 Hz) |

Figure 9:
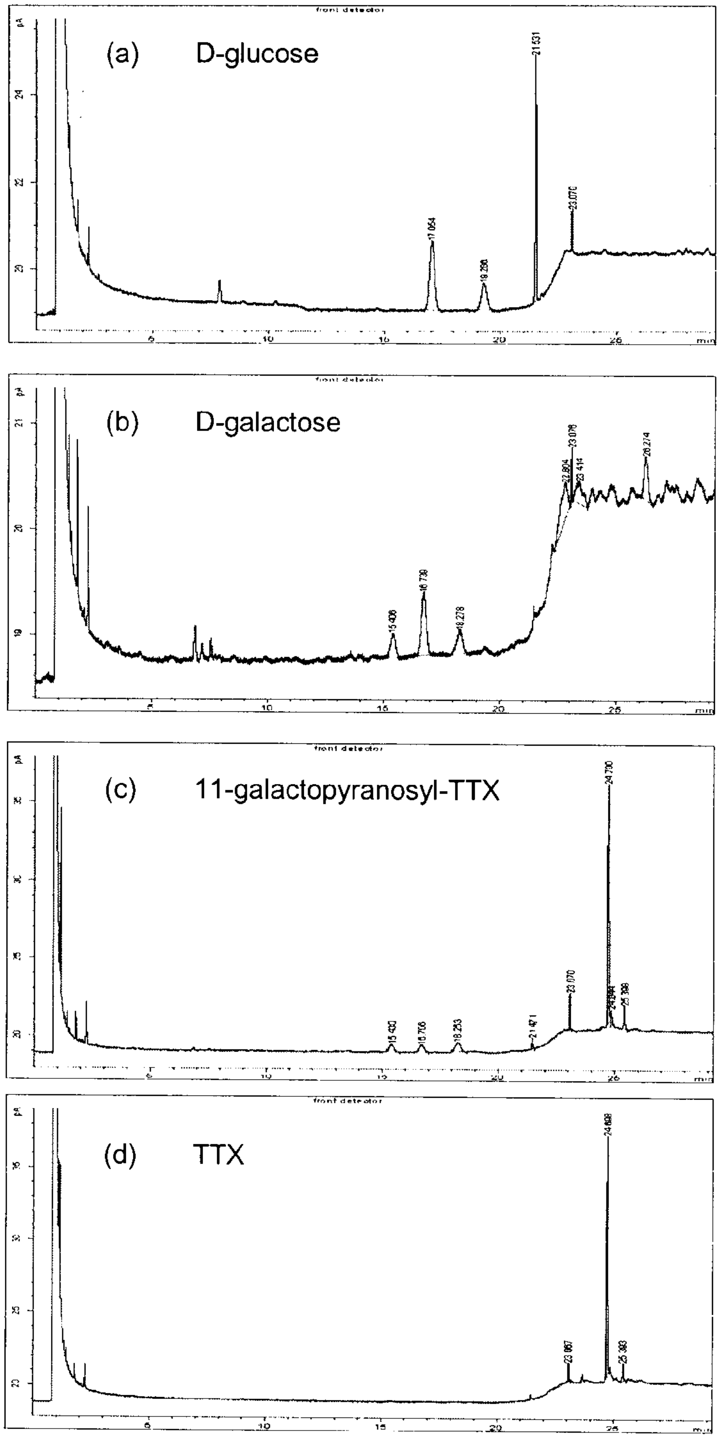
FIG. 9 illustrates the GC chromatograms of the degradation-derivatization products from (a) D-glucose (b) D-galactose, (c) 11-galactopyranosyl-TTX, and (d) Tetrodotoxin.

NOTE:
1. Solvent: 4% $CD_3COOD$ in $D_2O$
2. Proton signals of H-8, H-7, H-5 and H-9 are interchangeable GC Analysis of the Degradation-Derivatization Products:

"Impurity A", Tetrodotoxin, D-glucose and D-galactose were treated with 0.2 M HCl, followed by TMSCl and HMDS. The degradation-derivatization products were analyzed by GC. The GC chromatograms are shown in FIG. 9. A total of three peaks were detected in D-galactose while only two peaks were detected in D-glucose (FIG. 9*a* and FIG. 9*b*). The derivative GC method can clearly differentiate D-Glucose from D-Galactose.

FIG. 9*c* shows the GC chromatograms of degradation-derivatization products from "Impurity A". The number of peaks detected and their retention times completely match with that from D-galactose (FIG. 9*b*), suggesting that the sugar moiety in "Impurity A" is a galactoside. In a parallel experiment with TTX, no peak was detected, suggesting that the three peaks detected are derived from the hydrolyzed sugar moiety in "Impurity A". The study confirms that the sugar moiety in "Impurity A" is galactose, not glucose. This is consistent with the results of the NMR studies.

Because the analytical methods used are not able to distinguish whether the 11-galactopyranoside is a D-galactose or an L-galactose, the 11-sugar moiety in "Impurity A" can be either D-galactopyranoside or L-galactopyranoside, or could be mixtures thereof. Both structures in Formulae I-a and I-b, mixtures thereof, and naturally existing isomers of 11-galactopyranoside isolated from nature, are encompassed within the scope of this invention.

Biological Activities

Example 2

Evaluation of Effect of 11-Galactopyranosyl-TTX on the Acetic Acid-Induced Writhing Test in Mice Methods Sample Preparation:

The stock solution was prepared by dissolving the test sample in 0.02% dilute acetic acid solution. Various concentrations of solution were obtained by diluting the stock solution with 0.02% HOAc.

Mice (male and female) were acclimatized to testing environment (clear Plexiglas box) for 15 min or until explorative behaviour ceased. The animals were handled with care to minimize stress. The mice were assigned randomly to a blank negative control group, test sample group, or morphine positive control group.

The test articles (blank control, test sample, or morphine control) were delivered by a single intramuscular injection.

Thirty minutes after injection of test articles, the mice were injected i.p. in the lower left quadrant of abdomen with 0.2 ml/mouse of 1% acetic acid solution.

The number of writhes was counted over a period of 15 min beginning 5 min after injection of acetic acid. The writhing inhibition rate was calculated according to the following formula:

$$\text{Writhing inhibition rate}(\%) = \frac{\left(\begin{array}{c}\text{Average number of writhes}\\ \text{in control group}\end{array}\right) - \left(\begin{array}{c}\text{Average number of writhes}\\ \text{in treatment group}\end{array}\right)}{\begin{array}{c}\text{Average number of writhes}\\ \text{in control group}\end{array}} \times 100\%$$

$ID_{50}$ values and the 95% confidence intervals were calculated based on the Bliss calculation.

Results

The analgesic effect of 11-galactopyranosyl-TTX (gTTX or 11-Gal-TTX) was tested using the above method. Kunming mice, 18~22 g, both male and female, were used in the tests. The mice, general clean class, with quality certificate No SCXK-2003-0003, were obtained from the Experimental Animal Centre of Guangxi Medical University, Guangxi, China. The mice were fasted for 12 hours before all tests but water was provided ad libitum.

11-galactopyranosyl-TTX was tested at several concentrations (1.19, 2.38, and 4.75 μg/kg, i.m.). The results are shown in Table 3. The $ID_{50}$ value calculated for 11-Gal-TTX is 2.70 μg/kg, with a 95% confidence interval of 2.0-3.6 μg/kg.

TABLE 3

Dose response of 11-galactopyranosyl-TTX in the mouse writhing tests

| Group | Dose (μg/kg) | Number of animals | Number of writhes | Inhibition rate (%) |
|---|---|---|---|---|
| Control (blank) | — | 10 | 31.70 ± 4.7 | |
| 11-Gal-TTX | 1.19 | 10 | 22.10 ± 6.4*** | 30.3 |
| 11-Gal-TTX | 2.38 | 10 | 15.30 ± 6.4*** | 51.7 |
| 11-Gal-TTX | 4.75 | 10 | 12.50 ± 4.7*** | 60.6 |

***P < 0.001 compared to control group

The results show that the 11-galactopyranosyl-TTX has an inhibitory effect on pain.

The above-described embodiments of the present invention are intended to be examples only. Alterations, modifications and variations may be effected to the particular embodiments by those of skill in the art without departing from the scope of the invention, which is defined solely by the claims appended hereto.

What is claimed is:

1. An isolated or purified compound of Formula I, or a pharmaceutically acceptable salt, solvate, or hydrate form thereof, (I)

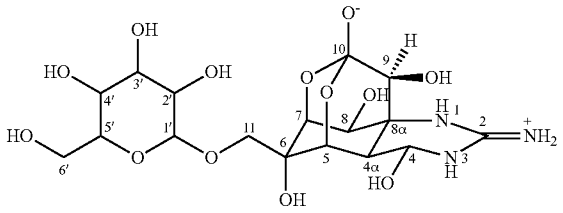

wherein the substituent at C-11 is a galactoside.

2. The compound of claim 1, wherein the isomeric form of the galactoside of said compound is D-galactoside.

3. The compound of claim 1, wherein the isomeric form of the galactoside of said compound is L-galactoside.

4. The compound of claim 1, wherein said compound has been isolated from a species selected from the group consisting of puffer fish, goby fish, newt, frogs, blue ringed octopus and marine algae.

5. The compound of claim 1, wherein said compound is isolated from puffer fish.

6. The compound of claim 1, wherein said compound is purified from a preparation of tetrodotoxin (TTX), wherein said TTX has been isolated from a species selected from the group consisting of puffer fish, goby fish, newt, frogs, blue ringed octopus and marine algae.

7. The compound of claim 1, wherein said compound is greater than 70% pure.

8. The compound of claim 1, wherein said compound is greater than 90% pure.

9. A pharmaceutical composition comprising the compound of claim 1, further admixed with one or more pharmaceutically acceptable excipient(s).

10. A method for treating pain, comprising administering a therapeutically effective amount of a compound of claim 1, to a subject in need thereof.

11. The method of claim 10, wherein said pain is neuropathic pain, visceral pain or somatic pain.

12. The method of claim 10, wherein said administration is systemic administration.

13. The method of claim 12, wherein said systemic administration is performed by intramuscular injection, subcutaneous injection, or intravenous injection.

14. A method for treating pain, comprising administering a therapeutically effective amount of a pharmaceutical composition according to claim 9, to a subject in need thereof.

15. The method of claim 14, wherein said pain is neuropathic pain, visceral pain or somatic pain.

16. The method of claim 15, wherein said administration is systemic administration.

17. The method of claim 16, wherein said systemic administration is performed by intramuscular injection, subcutaneous injection, or intravenous injection.

* * * * *

UNITED STATES PATENT AND TRADEMARK OFFICE

CERTIFICATE OF CORRECTION

PATENT NO. : 8,486,901 B2
APPLICATION NO. : 13/258529
DATED : July 16, 2013
INVENTOR(S) : Weiyang Lin It is certified that error appears in the above-identified patent and that said Letters Patent is hereby corrected as shown below:

Title page 1, item (73) ("Assignee"), delete "Wachai" and insert -- Wanchai --.

Title page 1, item (57) ("Abstract"), line 1, delete "tetrodotoxm" and insert -- tetrodotoxin --.

Signed and Sealed this
Twenty-ninth Day of October, 2013

Teresa Stanek Rea
*Deputy Director of the United States Patent and Trademark Office*

UNITED STATES PATENT AND TRADEMARK OFFICE

CERTIFICATE OF CORRECTION

| | |
|---|---|
| PATENT NO. | : 8,486,901 B2 |
| APPLICATION NO. | : 13/258529 |
| DATED | : July 16, 2013 |
| INVENTOR(S) | : Lin et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 108 days.

Signed and Sealed this
Second Day of December, 2014

Michelle K. Lee
*Deputy Director of the United States Patent and Trademark Office*